(12) United States Patent
Rosiwal et al.

(10) Patent No.: US 12,144,694 B2
(45) Date of Patent: Nov. 19, 2024

(54) FLEXIBLE ELECTRODE MADE OF A METAL BASE MATERIAL

(71) Applicant: BD-4 GMBH, Erlangen (DE)

(72) Inventors: Stefan Rosiwal, Bamberg (DE);
Matthias Karl, Waldmuenchen (DE);
Andreas Burkovski, Erlangen (DE);
Maximilian Goeltz, Moehrendorf (DE)

(73) Assignee: BD-4 GMBH, Erlangen (DE)

( * ) Notice: Subject to any disclaimer, the term of this patent is extended or adjusted under 35 U.S.C. 154(b) by 483 days.

(21) Appl. No.: 17/607,062

(22) PCT Filed: Apr. 6, 2020

(86) PCT No.: PCT/EP2020/059781
§ 371 (c)(1),
(2) Date: Oct. 28, 2021

(87) PCT Pub. No.: WO2020/221555
PCT Pub. Date: Nov. 5, 2020

(65) Prior Publication Data
US 2022/0226085 A1 Jul. 21, 2022

(30) Foreign Application Priority Data

Apr. 30, 2019 (EP) ..................................... 19171963

(51) Int. Cl.
*A61C 17/00* (2006.01)
*A61C 5/50* (2017.01)
(Continued)

(52) U.S. Cl.
CPC ................ *A61C 17/00* (2013.01); *A61C 5/50* (2017.02); *A61N 1/0548* (2013.01); *B08B 6/00* (2013.01)

(58) Field of Classification Search
CPC ........ A61C 17/00; A61C 5/50; A61N 1/0548; B08B 6/00
See application file for complete search history.

(56) References Cited

U.S. PATENT DOCUMENTS 11,090,486 B2* 8/2021 Becker ...................... A61C 5/44
2020/0046459 A1* 2/2020 Ng ............................ A61C 5/55

FOREIGN PATENT DOCUMENTS

CN 207646292 U 7/2018
EP 0994074 A2 4/2000
(Continued)

OTHER PUBLICATIONS

Alcaide et al. "Boron-Doped Nanocrystalline Diamond Electrodes for Neural Interfaces: In vivo Biocompatibility Evaluation" Frontiers in Neuroscience, vol. 10. Mar. 8, 2016.
(Continued)

*Primary Examiner* — Mark W. Bockelman
(74) *Attorney, Agent, or Firm* — Prismatic Law Group, PLLC

(57) ABSTRACT

The invention relates to a flexible electrode (8) made of a metal base material (10) with a coating (18) made of polycrystalline doped electrically conductive diamond and an intermediate layer (20) between the base material (10) and the coating (18), wherein the base material (10) is in the form of a needle or wire, wherein at least one circumferential, circular or spiral groove (12) is formed in the base material (10) about a longitudinal axis (17) of the base material (10).

22 Claims, 3 Drawing Sheets

Figure 1:
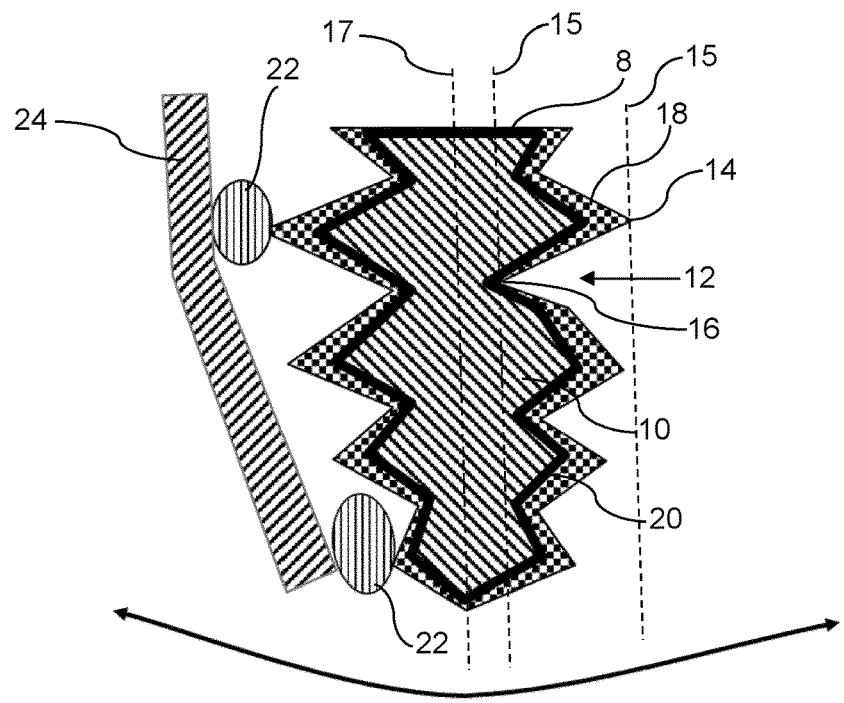

(51) Int. Cl.
*A61N 1/05* (2006.01)
*B08B 6/00* (2006.01)

(56) References Cited

FOREIGN PATENT DOCUMENTS

| WO | 2002045589 A2 | 6/2002 |
| WO | 2016017694 A1 | 2/2016 |

OTHER PUBLICATIONS

Ping et al. "Adhesive curing through low-voltage activation" Nature Communications 6:8050 I DOI: 10.1038/ncomms9050 Aug. 18, 2015.

Ochiai et al, "Application of Boron-Doped Diamond Microelectrodes for Dental Treatment with Pinpoint Ozone-Water Production" ChemPhysChem 14: 2094-2096 2013.

* cited by examiner

FLEXIBLE ELECTRODE MADE OF A METAL BASE MATERIAL

CROSS-REFERENCE TO RELATED APPLICATIONS

This application is a 371 National Phase of International Patent Application No. PCT/EP2020/059781 filed on Apr. 6, 2020, which claims priority to EP 19171963.2 filed on Apr. 30, 2019, the content of each of which applications is incorporated herein by reference.

The invention relates to a flexible electrode made of a metal base material with a coating made of polycrystalline doped electrically conductive diamond.

From Ochiai, T. et al., ChemPhysChem 2013, 14, pages 2094-2096, a boron-doped diamond microelectrode for dental treatment is known. The base material of the electrode is made of tungsten coated with boron-doped diamond using a microwave plasma-assisted chemical vapor deposition system. The electrode had a diameter of 500 µm and a polycrystalline diamond grain size of approximately 2 µm. The electrode was helically wrapped with a strip of Nafion® ion exchange membrane. A platinum wire was wound around the ion exchange membrane. When the electrode was used, the boron-doped diamond electrode was connected as anode and the platinum wire was connected as cathode. In the process, ozone, OH radicals and oxidative intermediate products were formed on the anode. These species have a disinfecting effect.

From WO 2016/017694, an electrically conductive coating material is known, which contains boron-doped diamond powder and an ion exchange resin dispersion. Moreover, an electrode in the form of a needle or disk coated with this coating material and the use of said electrode for treating caries and periodontitis and for treating the root canal are disclosed. As an advantage of the electrode, it is described that the coating does not readily peel off the electrode. For the use of the electrode, it is described that an electrolysis unit is used, which comprises, in addition to the mentioned electrode and a counter-electrode, an ion exchange membrane arranged between the electrode and the counter-electrode.

From Ping J. et al., Nat Commun. 2015; 6:8050, August 2015, a plastic cured by electrical activation is known.

The problem in the treatment of a root canal consists in that the root canal usually runs curved and is moreover commonly subdivided into multiple canals. Moreover, the surrounding hard tooth tissue has a high porosity. In order to achieve the most thorough possible disinfection of a root canal using an electrode coated with conductive diamond, said electrode should be introduced as deeply as possible into the tooth root. For this purpose, it is necessary that the electrode is flexible. However, a diamond coating applied directly to the electrode is in principle brittle and it peels off when the electrode is bent. Therefore, the aim of the present invention is to indicate a flexible electrode coated with conductive diamond, which is suitable, for example, for a root canal treatment.

This aim is achieved by the features of claim 1. Advantageous embodiments result from the features of claims 2 to 15.

The flexible electrode according to the invention comprises a metal base material with a coating made of polycrystalline doped electrically conductive diamond and an intermediate layer between the base material and the coating. The base material here is in the form of a needle, a wire or a strip. It can have a diameter or a maximum length of the diagonal through the cross-sectional area between 100 and 1000 µm, in particular between 200 and 800 µm, in particular between 300 and 600 µm.

In the base material, at least one circumferential, in particular circular or spiral, groove is formed in the base material about a longitudinal axis of the base material. The groove with the intermediate layer and the coating, i.e., the coated groove, can here be deeper than the sum of the maximum thickness of the coating and the maximum thickness of the intermediate layer. The depth of the coated groove is here measured between the highest point directly surrounding the coated groove and the lowest point of the coated groove. The highest point directly surrounding the coated groove can also lie in a region, not represented here, extending parallel to the longitudinal axis of the electrode. In this case, there is then a plurality of highest points directly surrounding the coated groove and located at the same height.

The depth of the coated groove and the maximum thickness of the coating and of the intermediate layer can be determined, for example, by electron microscopy. For this purpose, in an electron microscopy view of a section through the electrode, extending through the longitudinal axis of the electrode, auxiliary lines can be drawn parallel to the longitudinal axis of the electrode through the highest point directly surrounding the coated groove and the lowest point of the coated groove, and the spacing between these two lines can be determined. This spacing can then be considered to be the depth of the coated groove. If, in this way, the coated groove generated by means of a certain technique under certain conditions has a desired depth, it can be assumed that additional base material processed identically under identical conditions results in the same grooves. Alternatively, the depth of a groove can also be determined in a nondestructive manner by means of a scanning electron microscope, by X-ray radiation, by surface scanning with an electron beam or by light microscopy, for example using a confocal laser microscope. The layer thickness of the intermediate layer and of the coating can be predicted sufficiently satisfactorily by the selection of the parameters during the coating, so that no measurement is necessary in order to produce the electrode such that it has a coated groove that is deeper than the sum of the maximum thickness of the coating and of the maximum thickness of the intermediate layer. The effects of the parameters and their variation on the layer thickness of the coating and of the intermediate layer during the coating are well-known in the technology.

The groove can be formed in the base material, for example, by laser ablation with a short-pulse laser such as a Neodymium YAG laser and subsequent removal of oxides formed in the process by particle beams or by an acid. A mechanical structuring of the electrode surface by means of a grinding or pressing process or by particle beams is also possible. The particles used for the particle beams can be, for example, silicon carbide particles. For example, they can have a diameter in the range from 30 µm to 300 µm or less. The particles can be radiated onto the electrode, for example, with a pressure in the range from 3 bar or 5 bar or more.

The effect of the groove here consists in that as a result bending points in the base material are predetermined. In the case of one or more circumferential circular groove(s) or, in the case of a base material in the form of a strip, one or more rectangular groove(s), a segmentation of the electrode is achieved. The special feature in connection with the coating consists in that a bending of the electrode in the region of the groove(s) occurs, and there, in the coating, only small cracks form deep in the groove, which do not influence or at most only minimally influence the functionality of the electrode. In electrochemical measurements, it has been observed that the coating remains intact over more than 90% of its total area even after a bending of the electrode.

This results in an unprecedented flexibility of the electrode, enabling the introduction of said electrode deep into a curved running root canal of a tooth and the generation there of OH radicals and other disinfecting species, in order to enable an unprecedented thorough disinfection of the root canal.

The diamond can be doped with boron or phosphorus. The base material can be titanium, niobium, tantalum, iron, or an alloy containing these metals. The alloy can be Ti-6Al-4V, Ti-6Al-7Nb or another alloy containing, in addition to titanium, aluminum and/or niobium and/or iron and/or molybdenum. The base material can also be made of steel.

The intermediate layer can be made of a metal carbide, a metal nitride, a metal boride or a mixed compound containing at least two of the mentioned carbides. The intermediate layer can have a layer thickness of at most 10 µm, in particular at most 5 µm. The intermediate layer can moreover have a layer thickness of at least 50 nm, in particular at least 100 nm. Both the layer thickness of the intermediate layer and the layer thickness of the diamond can be influenced by the coating conditions. This is known, for example, from the dissertation of Neuerer, K. "Beeinflussung der Titankarbid-Schichtdicke bei der HFCVD-Diamantbeschichtung von Titan durch Oberflächenvorbehandlungen and Variation der Beschichtungsparameter" of the Technical Faculty of the University of Erlangen-Nuremberg, 2013. The electrode can be coated with diamond by hot filament chemical vapor deposition (HFCVD) or microwave plasma-assisted chemical vapor deposition (MPCVD) or another type of chemical vapor deposition (CVD) on the surface of the electrode in a vapor containing a boron compound.

In an embodiment, the coating with diamond has a layer thickness of at most 3 µm, in particular less than 2 µm, in particular less than 1 nm, and of at least 100 nm. Due to the small layer thickness, an additional flexibility of the electrode with nonetheless sufficient impermeability of the coating is achieved.

The invention moreover relates to an electrode according to the invention for use in an antimicrobial treatment of a microbially infected endodontium or periodontium of a tooth or of a microbially infected periimplant tissue of a mammal or human. The endodontium can be, in particular, a microbially infected root canal, and the periodontium can be in particular a microbially infected gum tissue, in particular in the region of the gingival pocket. The microbial infection can in particular be an infection caused by prokaryotes, in particular a bacterial infection, or caused by eukaryotes, in particular a mycosis.

In the treatment of a root canal, the electrode is introduced deep into the root canal. A counter-electrode can be arranged outside of the root canal. During the antimicrobial treatment, the electrode according to the invention is connected as anode, so that hydroxy radicals, ozone and, in particular in the case of the presence of chloride ions, additional antimicrobially active species such as, for example, chlorate ions ($ClO_3^-$), form. In the treatment of the root canal, said root canal can be filled with an electrolyte, for example, a physiological saline solution, if the root canal does not contain a physiological fluid which can generally be used as a natural electrolyte.

In the treatment of the microbially infected gingival pocket, the electrode according to the invention can also be introduced deep into the gingival pocket, and the counter-electrode can be arranged outside. Optionally, the gingival pocket can be rinsed with physiological saline solution, in order to provide an electrolyte. However, saliva is also suitable as a natural electrolyte.

In an embodiment of the electrode according to the invention, said electrode forms a double electrode with an additional electrode. Here, the additional electrode is also in the form of a needle, wire or strip. The additional electrode can be made of corrosion-resistant steel, for example. A coating of this electrode is not necessary. The electrode and the additional electrode can be interconnected in a region by at least one connection means or by a connection means and a spacer, so that thereby a direct or indirect electrical contact between the electrode and the additional electrode is excluded. The connection means and the spacer are therefore not electrically conductive. Moreover, the electrode and the additional electrode can be interconnected by the connection means or by the connection means and the spacer so that, over at least 80% of the length of the region between the electrode and the additional electrode, a free space to be occupied by an electrolyte during the treatment is ensured, wherein a spacing between the electrode and the additional electrode within this space is between 40 µm and 300 µm. The region is here limited by the respective outermost sites at which the electrode and the additional electrode are interconnected by the connection means. As a result of the small spacing between the electrode and the additional electrode and due to the fact that this space is free and in particular no ion exchange membrane is provided there, a highly efficient generation of OH radicals with relatively low current flow is achieved. The efficiency is higher than in the case of a diamond-coated electrode separated from the counter-electrode by an ion exchange membrane. Here, the electrode must have a coating with polycrystalline doped electrically conductive diamond on its surface at least within the region.

The additional electrode can also be designed to be very thin, so that the double electrode formed overall also has only a small maximum diameter, and, as a result, microbially infected gingival pockets and possibly sufficiently wide root canals can be treated satisfactorily thereby. During the treatment, the electrode can be connected as anode and the additional electrode can be connected as cathode. For a treatment in dentistry or in jaw surgery, the electrode and optionally also the additional electrode can be held by an instrument holder, in particular an instrument holder for dentistry or jaw surgery, and supplied with current.

In an embodiment of the electrode according to the invention, which forms a double electrode with the additional electrode, the additional electrode is made of the same base material as the electrode and has the same structure as the electrode. In this case, the additional electrode is also coated with diamond. Thereby, a flexible double electrode can be provided, which, during the treatment, can be operated with reversed polarity or with alternating current. Thereby, the formation of deposits on the anode, which can reduce the efficiency of the anode and under some circumstances even cause a short circuit between the two electrodes, can be avoided. For this purpose, during the treatment, the electrode and the additional electrode are each alternatingly connected as anode and the respective other electrode as cathode. Moreover, due to the reversed polarity and the associated gas formation on the cathode which previously was connected as anode, the distribution of the OH radicals formed and of other antimicrobially active species is improved.

In an embodiment of the electrode which forms a double electrode with the additional electrode, the spacing between the electrode and the additional electrode within the space is between 40 and 200 μm, in particular between 40 and 110 μm.

The smaller the spacing is, the smaller the current intensities required for achieving the effect are and the more efficiently OH radicals are formed.

The connection means can be an electrically insulating adhesive, in particular an epoxy resin, or a nonconductive diamond. The spacer can be Teflon, a plastic filament or a wire with an electrically insulating coating. The plastic filament can be a polyethylene filament in particular a Teflon-coated polyethylene filament, made in particular of polyethylene having an ultra high molecular weight.

A double electrode connected by means of electrically nonconductive diamond as connection means can be produced, for example, as follows:

The diamond-coated flexible electrode according to the invention is coated with copper or wrapped with copper film at all the sites where no connection means is to be formed. The copper layer can have a thickness of approximately 5-50 μm. It can be generated, for example, by sputtering. During sputtering, regions which are not to be coated can be kept free by means of a mask or by covering. For the production of the double electrode, the coating or the covering with copper is interrupted in each case every 1 mm to 5 mm for in each case 0.1 mm to 1 mm, so that the diamond layer is exposed at these sites.

Subsequently, the additional electrode made of metal is secured by means of a copper foil on the flexible electrode so that the copper-covered and the non-copper-covered regions coincide. As a result, the copper-free regions of the two electrodes face each other exactly at a spacing of 5-50 μm. The additional electrode can be made of titanium, niobium, tantalum or steel with a TiNB intermediate layer or made of a metal coated with polycrystalline doped electrically conductive diamond. It can also be a flexible diamond-coated electrode according to the invention. If the additional electrode is not diamond-coated, then it is seeded with nanodiamond, for example, by HFCVD, MPCVD or CVD. This can occur before or after the securing on the flexible electrode. Here it is important that the non-copper-covered regions are seeded.

The formation of the connection made of nonconductive diamond occurs by CVD of diamond without boron. Here the opposite exposed regions on the electrodes merge. Thereby, electrically nonconductive, mechanically firm connections between the electrodes form. The minimum layer thickness of the nonconductive diamond layer corresponds to half the electrode spacing. It is approximately in the range from 5 μm to 50 μm.

Finally, the copper foil is mechanically removed. Copper coatings generated by sputtering are removed by etching with an acid. Thereby, the opposite electrically active regions of the double electrode are exposed.

After the antimicrobial treatment, the treatment of the microbially infected endodontium can comprise an at least partial filling of a cavity existing in the tooth or formed as result of another treatment, for example, drilling of the root canal, with a plastic cured by electrical activation in the cavity. Here, the electrical activation occurs by means of the electrode in the cavity.

The cavity can also be a drilled root canal or simply a root canal from which biological material contained therein has been removed, optionally with the small dentin canals leading into the root canal.

The plastic can be, for example, a polyamidoamine-g-diazirine. The plastic is known, for example, from Ping J. et al., Nat. Commun. 2015; 6:8050, August 2015. For the electrical activation, the electrode according to the invention is used with a counter-electrode. Since the initiation and the progression of the crosslinking of the plastic occur as a function of voltage and time, the curing by electrical activation can be controlled very satisfactorily.

The treatment can also comprise an at least partial filling of the cavity with an inorganic substance, the precipitation of which from a solution in the cavity is initiated by anodic oxidation. Here, the anodic oxidation occurs by means of the electrode. For this purpose, a counter-electrode can be arranged outside of the tooth or likewise in the cavity, for example when the above-described double electrode is used. For the precipitation, for example, a phosphonate such as, for example, a metal diethyl phosphonate, in particular aluminum diethyl phosphonate, can be converted into an insoluble orthophosphate by anodic oxidation by means of the electrode according to the invention. The precipitation can be reinforced by a chemical reaction. For this purpose, the orthophosphate can be reacted, for example, with a metal halide, in particular a metal chloride, in particular iron(III) chloride ($FeCl_3$). Thereby, the corresponding metal phosphate, for example, iron(III) phosphate, is then precipitated.

Both when filling with plastic and when filling with inorganic substance, a partial filling can suffice. Here, it can suffice if thereby the small dentin canals are closed, so that microorganisms can no longer penetrate therefrom into the root canal.

Below, the invention is explained in further detail based on embodiment examples.

Figure 2:
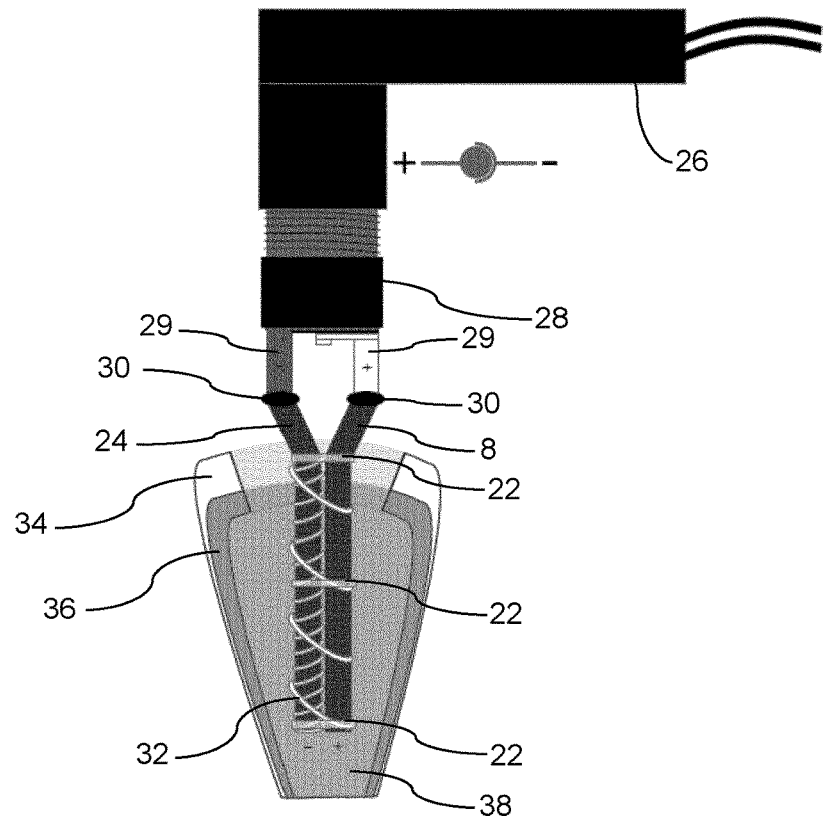
Figure 3:
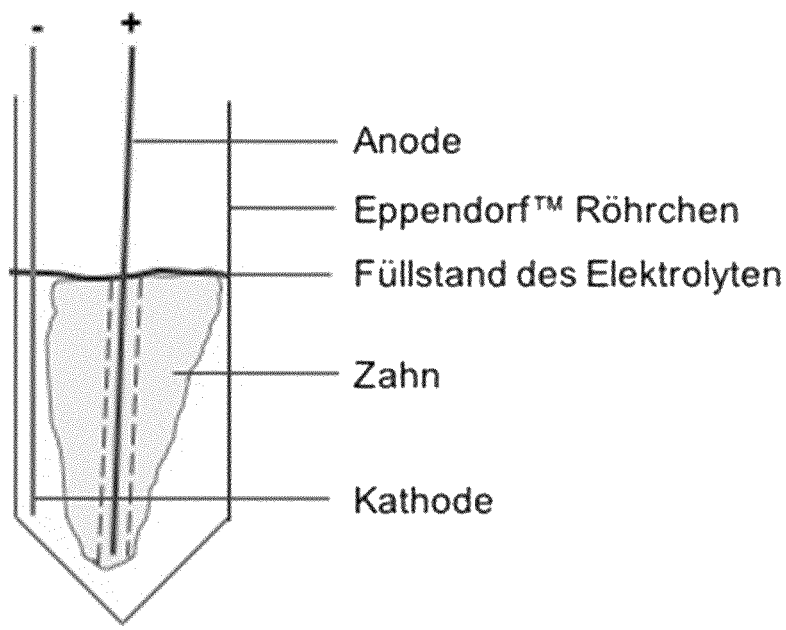
Figure 4:
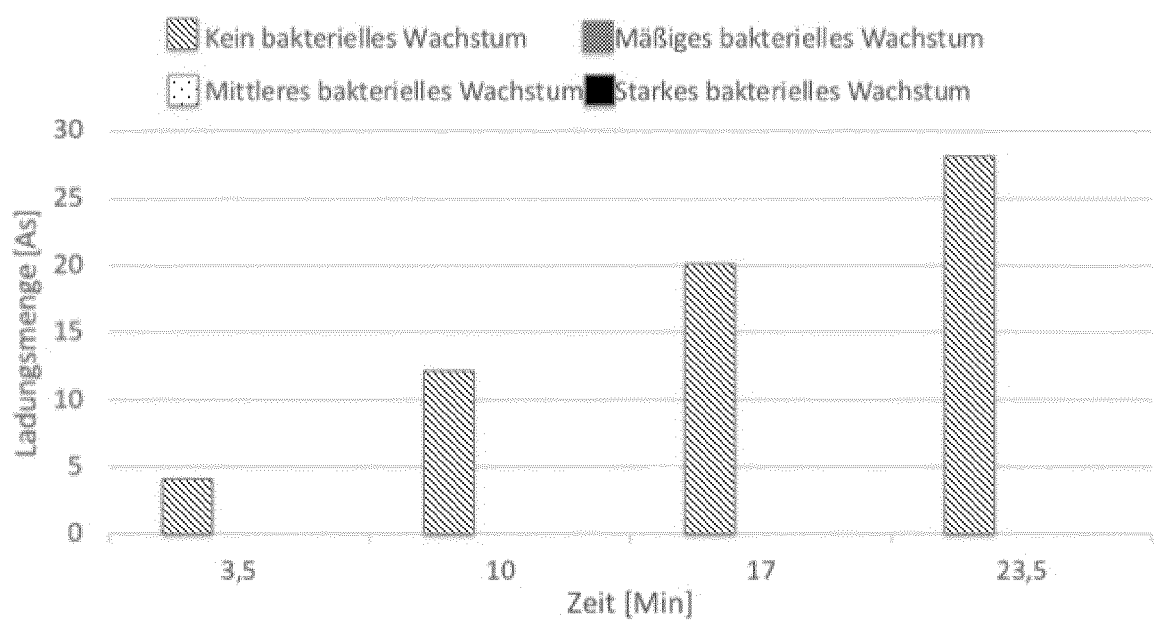
Figure 5:
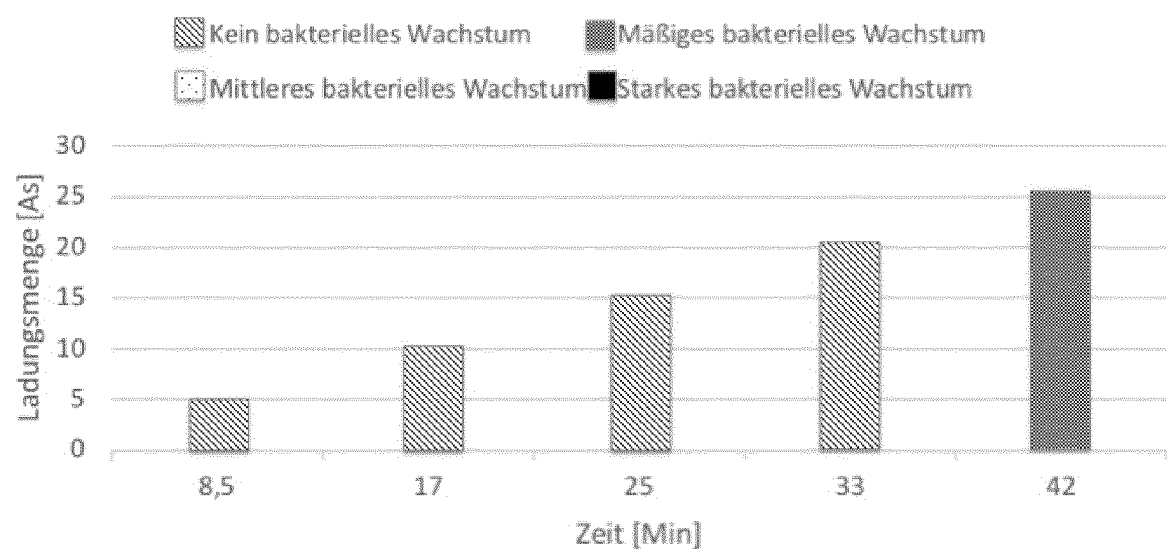

The figures show:

FIG. 1 a diagrammatic representation of an electrode according to the invention, which forms a double electrode with an additional electrode, FIG. 2 a diagrammatic representation of a tooth and a dentistry instrument holder with an electrode according to the invention held thereby and supplied with current, as a component of a double electrode, FIG. 3 a diagrammatic cross-sectional representation of an experimental setup for inactivating *Staphylococcus epidermidis* and *Bacillus subtilis* in a drilled root canal of a human tooth, FIG. 4 a diagram showing the dependency of the growth of *Staphylococcus epidermidis* on the charge quantity and on the duration of the treatment of the root canal, and FIG. 5 a diagram showing the dependency of the growth of *Bacillus subtilis* on the charge quantity and the duration of the treatment of the root canal.

In FIG. 1, a greatly enlarged diagrammatic cross section through the tip of an electrode 8 according to the invention in the form of a needle is shown. The electrode consists, inter alia, of the base material 10 which comprises grooves 12. During the coating with the coating 18 made of doped diamond, the intermediate layer 20 is formed directly on the base material 10. As an example, 14 marks a highest point directly surrounding the coated groove and 16 marks a deepest point of the coated groove. For the measurement of the depth of the coated groove, auxiliary lines 15 can be drawn through the highest point 14 directly surrounding the coated groove and the deepest point 16, parallel to the longitudinal axis 17 of the electrode 8. The spacing between these two lines represents the depth of the groove 12. The highest point 14 directly surrounding the coated groove 12 can also lie in a region, not represented here, extending parallel to the longitudinal axis 17. In this case, a plurality of highest points 14 directly surrounding the coated groove 12 and located at the same height then exists. The sum of the maximum thickness of the coating 18 and of the intermediate layer 20 is smaller than the depth of the coated groove 12. The electrode 8 is connected by a connection means 22, for example, by an adhesive or by a nonconductive diamond, to an additional electrode 24. Both the additional electrode 24 and the electrode 8 are flexible. Because the connection means 22 interconnects the two electrodes 8, 24 only at a few points, the flexibility of the double electrode formed by the electrode 8 and the additional electrode 24 is ensured by the connection. The additional electrode 24 can be made of steel, for example. The double arrow represented below the electrode 8 symbolizes the flexibility of the electrode.

FIG. 2 diagrammatically shows a handle 26 of a dentistry instrument which provides a current connection to a base 28. The base 28 has electrical contacts 29 on which the electrode 8 and the additional electrode 24 have been secured by soldering via the soldering sites 30. In the present case, both the electrode 8 and the additional electrode 24 are designed as electrodes according to the invention with a coating 18 with electrically conductive boron-doped diamond. The electrode 8 is here connected as anode. The additional electrode 24 connected as cathode is wrapped with a Teflon-coated polyethylene filament 32 made of polyethylene having an ultra high molecular weight. The Teflon coating here reduces the friction on the diamond coating and thus the mechanical stressing thereof. The wrapping is used here as spacer. A portion of the polyethylene filament 32 also is wrapped around the electrode 8 and used for the immobilization when the connection means 22 is attached. The connection means 22 can be a cyanoacrylate adhesive, for example. The double electrode thus formed by the electrode 8 and the additional electrode 24 is introduced into the root canal 38 of a tooth which is represented diagrammatically here. It can be energized here and, in the process, it releases OH radicals and other microbially active species.

Preparation of an Agar Growth Medium

Liquid Standard 1 nutrient growth medium (St. 1) with agar-agar is referred to below as St. 1 agar. The components of this St. 1 agar are listed in the following Table 1.

TABLE 1

Ingredients of Standard 1 agar nutrient growth medium in 400 mL demineralized water

| Ingredients | Quantity [g] | Manufacturer/article number |
| --- | --- | --- |
| Glucose monohydrate | 0.44 | Carl Roth GmbH/6780.1 |
| Sodium chloride | 2.34 | Carl Roth GmbH/3957.1 |
| Agar-agar | 8.00 | Carl Roth GmbH/5210.3 |
| Yeast extract | 1.20 | Carl Roth GmbH/2363.3 |
| Peptone from casein | 6.00 | Merck KGaA/1.02239.0500 |

The pH was adjusted to 7.4 by addition of sodium hydroxide. The St. 1 agar plated in petri dishes solidified after a few minutes and was used as growth medium.

Inactivation of *Staphylococcus epidermidis* and *Bacillus subtilis* in a Drilled Root Canal of a Human Tooth Extracted human teeth with drilled root canal were obtained from a dentist. The teeth were first incubated for at least 20 hours in a physiological saline solution containing *Staphylococcus epidermidis* or *Bacillus subtilis*. Here, the root canals were colonized with the respective bacteria. Subsequently, the teeth were rinsed with physiological saline solution and arranged in physiological saline solution as electrolyte, in the experimental setup shown in FIG. 3.

The anode designed as electrode according to the invention here consisted of a niobium wire coated with boron-doped diamond and the cathode consisted of steel. A voltage in the range from 5 to 9 volt was applied, so that the current intensities indicated in FIGS. 4 and 5 flowed in the respective indicated treatment time.

After the respective indicated treatment time, the respective tooth was split, and the resulting inner split surfaces comprising the surface of the root canal were pressed repeatedly onto an St. 1 agar growth medium and then placed with this surface on the agar. The agar growth medium was then incubated at 27 degrees for 1-2 days. Bacterial growth could be detected by the formation of colonies. The colonies were detectable as dots with the naked eye and they were classified subjectively as no growth, moderate growth, medium growth and strong bacterial growth.

Inactivation of *Staphylococcus epidermidis*

The results which can be seen in FIG. 4 show that already at a current quantity of 4 As, corresponding to a treatment time of 3.5 minutes, a complete sterilization of the inner root canal surface was achieved. Bacterial growth was found on none of the agar growth media.

Inactivation of the *Bacillus subtilis*

The results which can be seen in FIG. 5 show that with a current quantity of 5 As, corresponding to a treatment time of 8.5 minutes, a complete sterilization of the inner root canal surface was already observed. A moderate bacterial growth appearing after a treatment time of 42 minutes and a current quantity of 25 As may have been caused by the ability of the *Bacillus subtilis* to form spores and the possible presence of these spores in the small dentin canals of the tooth root. Furthermore, it was observed that, in the case of spore formation, the charge quantity necessary for complete sterilization can be more than one hundred times higher.

The tests carried out on the extracted tooth show that an electrode according to the invention, coated with boron-doped diamond and connected as anode, is well suited for disinfecting a root canal in a relatively short time. Such an anode can be introduced for this purpose during a tooth treatment into an opened root canal and energized. The cathode necessary for this purpose can be arranged in the vicinity of the tooth to be treated within the oral cavity. Alternatively, the electrode according to the invention can be designed as part of a double electrode which, as such, can be introduced into the root canal, as diagrammatically shown in FIG. 2.

LIST OF REFERENCE NUMERALS

8 Electrode
10 Base material
12 Groove
14 Highest point directly surrounding the coated groove
15 Auxiliary line
16 Deepest point
17 Longitudinal axis
18 Coating
20 Intermediate layer
22 Connection means
24 Additional electrode
26 Handle
28 Base
29 Electrical contact
30 Soldering site
32 Polyethylene filament
34 Dental enamel 36 Dentin
38 Root canal

The invention claimed is:

1. A flexible electrode made of a metal base material with a coating made of polycrystalline doped electrically conductive diamond and of an intermediate layer between the base material and the coating, wherein the base material is in the form of a needle, wire or strip, wherein at least one circumferential groove is formed in the base material about a longitudinal axis of the base material.

2. The flexible electrode according to claim 1, wherein the groove with the intermediate layer and with the coating is deeper than the sum of the maximum thickness of the coating and of the maximum thickness of the intermediate layer.

3. The flexible electrode according to claim 1, wherein the diamond is doped with boron or phosphorus.

4. The flexible electrode according to claim 1, wherein the base material is made of titanium, niobium, tantalum, iron, or an alloy containing these metals or of steel.

5. The flexible electrode according to claim 1, wherein the intermediate layer is made of a metal carbide, a metal nitride, a metal boride or a mixed compound containing at least two of the mentioned carbides.

6. The flexible electrode according to claim 4, wherein the intermediate layer has a layer thickness of at most 10 μm.

7. The flexible electrode according to claim 1, wherein the coating with diamond has a layer thickness of at most 3 μm.

8. The flexible electrode according to claim 1 for use in an antimicrobial treatment of a microbially infected endodontium or periodontium of a tooth or of a microbially infected periimplant tissue of a mammal or human.

9. The flexible electrode according to claim 8 wherein the electrode forms a double electrode with an additional electrode, wherein the additional electrode is also in the form of a needle, a wire or a strip, wherein the electrode and the additional electrode are interconnected in a region by at least one connection means or by a connection means and a spacer, so that thereby an electrical contact between the electrode and the additional electrode is excluded and, over at least 80% of the length of this region between the electrode and the additional electrode, a free space to be occupied during the treatment by an electrolyte is ensured, wherein a spacing between the electrode and the additional electrode within this space is between 40 μm and 300 μm.

10. The flexible electrode according to claim 9, wherein, during the treatment, the electrode is connected as anode and the additional electrode is connected as cathode.

11. The flexible electrode according to claim 9, wherein the additional electrode is made of the same base material as the electrode and has the same structure as the electrode.

12. The flexible electrode according to claim 11, wherein, during the treatment, the electrode and the additional electrode are each alternatingly connected as anode and the respective other of the two electrodes is connected as cathode.

13. The flexible electrode according to claim 9, wherein the spacing between the electrode and the additional electrode within the space is between 40 μm and 200 μm.

14. The flexible electrode according to claim 9, wherein the connection means is an electrically insulating adhesive, and the spacer is Teflon or a wire with an electrically insulating coating.

15. A method of treatment, comprising administering the flexible electrode according to claim 1 in an antimicrobial treatment of a microbially infected endodontium or periodontium of a tooth or of a microbially infected periimplant tissue of a mammal or human.

16. The method of claim 15, wherein the treatment of the microbially infected endodontium after the antimicrobial treatment comprises an at least partial filling of a cavity existing in the tooth or formed by another treatment, with a plastic cured by electrical activation in the cavity or with an inorganic substance, the precipitation of which from a solution in the cavity is initiated by anodic oxidation, wherein the activation or the anodic oxidation occurs by means of the electrode in the cavity.

17. The flexible electrode according to claim 4, wherein the intermediate layer has a layer thickness of at most 5 μm.

18. The flexible electrode according to claim 4, wherein the intermediate layer has a layer thickness of at least 50 μm.

19. The flexible electrode according to claim 1, wherein the coating with diamond has a layer thickness of less than 2 μm.

20. The flexible electrode according to claim 1, wherein the coating with diamond has a layer thickness of at least 100 μm.

21. The flexible electrode according to claim 9, wherein the spacing between the electrode and the additional electrode within the space is between 40 μm and 110 μm.

22. The flexible electrode according to claim 14, wherein the electrically insulating adhesive is an epoxy resin, a plastic filament, or a nonconductive diamond.

* * * * *

UNITED STATES PATENT AND TRADEMARK OFFICE
CERTIFICATE OF CORRECTION

PATENT NO. : 12,144,694 B2
APPLICATION NO. : 17/607062
DATED : November 19, 2024
INVENTOR(S) : Stefan Rosiwal et al.

It is certified that error appears in the above-identified patent and that said Letters Patent is hereby corrected as shown below:

In the Claims

In Column 10, Line 13, in Claim 14, after "adhesive," insert -- a plastic filament, or a nonconductive diamond --.

In Column 10, Lines 45-46, in Claim 22, delete ", a plastic filament, or a nonconductive diamond".

Signed and Sealed this
Eighteenth Day of March, 2025

Coke Morgan Stewart
*Acting Director of the United States Patent and Trademark Office*